(12) United States Patent
Molt et al.

(10) Patent No.: US 8,410,270 B2
(45) Date of Patent: Apr. 2, 2013

(54) TRANSITION METAL COMPLEXES AND USE THEREOF IN ORGANIC LIGHT-EMITTING DIODES V

(75) Inventors: Oliver Molt, Hirschberg (DE); Christian Lennartz, Schifferstadt (DE); Evelyn Fuchs, Mannheim (DE); Korinna Dormann, Bad Duerkheim (DE); Nicolle Langer, Heppenheim (DE); Christian Schildknecht, Mannheim (DE); Jens Rudolph, Worms (DE); Gerhard Wagenblast, Wachenheim (DE); Soichi Watanabe, Mannheim (DE)

(73) Assignee: BASF SE, Ludwigshafen (DE)

( * ) Notice: Subject to any disclaimer, the term of this patent is extended or adjusted under 35 U.S.C. 154(b) by 189 days.

(21) Appl. No.: 12/997,000

(22) PCT Filed: Jun. 9, 2009

(86) PCT No.: PCT/EP2009/057089
§ 371 (c)(1),
(2), (4) Date: Dec. 9, 2010

(87) PCT Pub. No.: WO2009/150151
PCT Pub. Date: Dec. 17, 2009

(65) Prior Publication Data
US 2011/0087026 A1    Apr. 14, 2011

(30) Foreign Application Priority Data
Jun. 10, 2008   (EP) .................................... 08157913

(51) Int. Cl.
*C07F 15/00* (2006.01)
*H01L 51/50* (2006.01)
(52) U.S. Cl. ........................ 546/10; 428/690; 313/504
(58) Field of Classification Search .................... 546/10; 428/690; 313/504
See application file for complete search history.

(56) References Cited

U.S. PATENT DOCUMENTS

| | | | |
|---|---|---|---|
| 2002/0076576 A1 | 6/2002 | Li et al. | |
| 2003/0129439 A1 | 7/2003 | Li et al. | |
| 2003/0134140 A1 | 7/2003 | Li et al. | |
| 2003/0138657 A1 | 7/2003 | Li et al. | |
| 2007/0108891 A1 | 5/2007 | Watanabe | |
| 2007/0196690 A1 | 8/2007 | Ikemizu et al. | |
| 2008/0297033 A1 | 12/2008 | Knowles et al. | |

FOREIGN PATENT DOCUMENTS

| | | |
|---|---|---|
| EP | 1 372 360 | 12/2003 |
| EP | 1 617 710 | 1/2006 |
| EP | 1 617 711 | 1/2006 |
| WO | 02 15645 | 2/2002 |
| WO | 02 47440 | 6/2002 |
| WO | 2004 095889 | 11/2004 |
| WO | 2005 019373 | 3/2005 |
| WO | 2005 113704 | 12/2005 |
| WO | 2005 123873 | 12/2005 |
| WO | 2006 018292 | 2/2006 |
| WO | 2006 056418 | 6/2006 |
| WO | 2006 067074 | 6/2006 |
| WO | 2006 096951 | 9/2006 |
| WO | 2006 106842 | 10/2006 |
| WO | 2006 112265 | 10/2006 |
| WO | 2006 121811 | 11/2006 |
| WO | 2006 130598 | 12/2006 |
| WO | 2007 018067 | 2/2007 |
| WO | 2007 058080 | 5/2007 |
| WO | 2007 058255 | 5/2007 |
| WO | 2007 069542 | 6/2007 |
| WO | 2007 093282 | 8/2007 |
| WO | 2007 095118 | 8/2007 |
| WO | 2007 115970 | 10/2007 |
| WO | 2007 115981 | 10/2007 |
| WO | 2008 000726 | 1/2008 |
| WO | 2008 000727 | 1/2008 |
| WO | 2008 034758 | 3/2008 |
| WO | 2008 058104 | 5/2008 |
| WO | 2008 156879 | 12/2008 |

OTHER PUBLICATIONS

International Search Report issued Aug. 27, 2009 in PCT/EP09/057089 filed Jun. 9, 2009.
Baldo, M.A., et al., "Very high-efficiency green organic light-emitting devices based on electrophosphorescence," Applied Physics Letters, vol. 75, No. 1, pp. 4-6, (Jul. 5, 1999).
Atzrodt, J., et al., "The Renaissance of H/D Exchange," Angew. Chem. Int. Ed., vol. 46, pp. 7744-7765, (2007).
U.S. Appl. No. 12/997,378, filed Dec. 10, 2010, Molt, et al.
U.S. Appl. No. 12/997,380, filed Dec. 10, 2010, Molt, et al.
U.S. Appl. No. 13/516,117, filed Aug. 27, 2012, Molt, et al.

*Primary Examiner* — Charanjit Aulakh
(74) *Attorney, Agent, or Firm* — Oblon, Spivak, McClelland, Maier & Neustadt, L.L.P.

(57) ABSTRACT

Metal complexes comprising at least one polycyclic aromatic ligand and bearing at least one deuterium atom, an organic light-emitting diode comprising at least one inventive metal complex, a light-emitting layer comprising at least one inventive metal complex, an organic light-emitting diode comprising at least one inventive light-emitting layer, the use of the at least one inventive metal complex in organic light-emitting diodes, and a device selected from the group consisting of stationary visual display units such as visual display units of computers, televisions, visual display units in printers, kitchen appliances and advertising panels, illuminations, information panels and mobile visual display units such as visual display units in cellphones, laptops, digital cameras, vehicles, and destination displays on buses and trains, comprising at least one inventive organic light-emitting diode.

17 Claims, No Drawings

TRANSITION METAL COMPLEXES AND USE THEREOF IN ORGANIC LIGHT-EMITTING DIODES V

The present invention relates to metal complexes comprising at least one polycyclic aromatic ligand, said metal complexes bearing at least one deuterium atom, an organic light-emitting diode comprising at least one inventive metal complex, a light-emitting layer comprising at least one inventive metal complex, an organic light-emitting diode comprising at least one inventive light-emitting layer, the use of the at least one inventive metal complex in organic light-emitting diodes, and a device selected from the group consisting of stationary visual display units such as visual display units of computers, televisions, visual display units in printers, kitchen appliances and advertising panels, illuminations, information panels and mobile visual display units such as visual display units in cell phones, laptops, digital cameras, vehicles, and destination displays on buses and trains, comprising at least one inventive organic light-emitting diode.

Organic light-emitting diodes (OLEDs) exploit the propensity of materials to emit light when they are excited by electrical current. OLEDs are of particular interest as an alternative to cathode ray tubes and to liquid-crystal displays for producing flat visual display units. Owing to the very compact design and the intrinsically low power consumption, devices comprising OLEDs are suitable especially for mobile applications, for example for applications in cellphones, laptops, etc.

The basic principles of the way in which OLEDs work and suitable structures (layers) of OLEDs are specified, for example, in WO 2005/113704 and the literature cited therein.

The light-emitting materials (emitters) used may, as well as fluorescent materials (fluorescence emitters), be phosphorescent materials (phosphorescence emitters). The phosphorescence emitters are typically organometallic complexes which, in contrast to the fluorescence emitters which exhibit singlet emission, exhibit triplet emission (M. A. Baldo et al., Appl. Phys. Lett. 1999, 75, 4 to 6). For quantum-mechanical reasons, when the phosphorescence emitters are used, up to four times the quantum efficiency, energy efficiency and power efficiency is possible. In order to implement the advantages of the use of the organometallic phosphorescence emitters in practice, it is necessary to provide phosphorescence emitters which have a high operative lifetime, a good efficiency, a high stability to thermal stress and a low use and operating voltage.

In order to satisfy the aforementioned requirements, numerous phosphorescence emitters have been proposed in the prior art.

For instance, WO 2007/095118 relates to metal complexes of cyclometalated imidazo[1,2-f]phenanthridine and diimidazo[1,2-A:1',2'-C]quinazoline ligands, and also isoelectronic and benzofused derivatives thereof. The metal complexes are phosphorescent and are used in OLEDs. According to WO 2007/095118, the OLEDs exhibit a long-lived and efficient blue, green and red emission. Deuterated systems are not mentioned in WO 2007/095118.

WO 2007/093282 mentions a specific electronic component and a process for production thereof and the use thereof. This electronic component may, for example, be an OLED. According to the description in WO 2007/093282, the electronic component comprises chemically reactive materials, which are electroluminescent materials or laser materials. The reactive materials include organometallic complexes which are capable of phosphorescence (J). These organometallic complexes include organometallic complexes of the formula (T) $[M(L)_n(L')_m(L'')_o]$ which may have a substructure $M(L)_n$ of the formula (U)

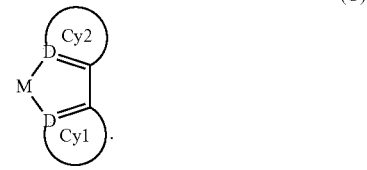

The Cy1 and Cy2 cycles may be substituted by R radicals, where R may be deuterium among other radicals. Examples of compounds of the formula (T) which comprise structural units of the formula (U) are not mentioned in WO 2007/093282. Furthermore, it is not evident from WO 2007/093282 whether metal complexes of the formula (T) which comprise structural units of the formula (U) where one of the Cy1 and Cy2 cycles is substituted by deuterium are advantageous for use in OLEDs.

EP-A 1 372 360 relates to organic electroluminescent polymers with improved stability. The polymers used are poly (phenylenevinylenes). In order to further improve the stability of the vinyl bonds in the poly(phenylenevinylenes) along the conjugated polymer chain, according to EP-A 1 372 360, poly(phenylenevinylenes) which have deuterium substitution on the vinylene moiety are used. The reason for the use of deuterated polymers is thus, according to EP-A 1 372 360, the stabilization of the reactive vinylene double bonds of the poly(phenylenevinylenes).

WO 02/47440 A1 discloses organic semiconductor materials in which one or more hydrogen atoms are replaced by deuterium. The organic semiconductors have a high luminescence and a good thermal stability. It is claimed that optoelectronic elements which comprise the organic semiconductors have improved performance and lifetime. The organic semiconductors are preferably luminescent organic polymers or organometallic compounds. The description mentions a large number of different organic semiconductor materials. The examples in WO 02/47440 A1 mention that an organic light-emitting diode which comprises fully deuterated $Ir(ppy)_3$-d8 as an emitter material has a higher quantum efficiency and luminance than an organic light-emitting diode which comprises nondeuterated $Ir(ppy)_3$ as an emitter material.

The results disclosed in WO 02/47440 A1 correspond to the results disclosed in WO 2006/095951 A1. WO 02006/095951 A1 discloses deuterated phosphorescent Ir complexes

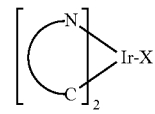

in which X is a bidentate ligand and the use thereof as an emitter material in OLEDs. OLEDs which comprise these deuterated complexes as an emitter material have, according to WO 2006/095951 A1, a higher quantum efficiency and luminance than OLEDs which comprise the corresponding nondeuterated Ir complexes as an emitter material.

With respect to the aforementioned prior art, it is an object of the present invention to provide further metal complexes suitable for phosphorescence for use in OLEDs, which exhibit a balanced spectrum of properties, for example good efficiencies, an improved lifetime and higher stabilities in the device, and also good charge transport properties and thermal stability. At the same time, especially phosphorescence emitters which enable an improved lifetime of the OLEDS are to be provided.

This object is achieved by a metal complex comprising at least one ligand of the general formula (I)

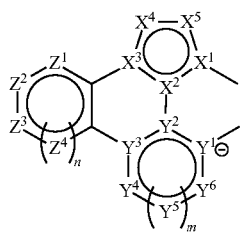

(I)

in which the symbols are each defined as follows:

$Y^5, Z^4$
  are each independently CD, $CR^1$, CH, N;
$X^1, X^2, X^3, Y^1, Y^2, Y^3$
  are each independently N or C;
$X^4, X^5$
  are each independently CD, $CR^1$, CH, N, S or O; where $X^4$ or $X^5$ may additionally be $NR^1$ when the other $X^5$ or $X^4$ radical in each case is N, CH, CD or $CR^1$;
$Y^4, Y^6$
  are each independently CD, $CR^1$, CH, N; where $Y^4$ or $Y^6$, in the case that m=0, may additionally be S, O or $NR^1$;
$Z^1, Z^2, Z^3$
  are each independently CD, $CR^1$, CH, N; where $Z^1, Z^2$ or $Z^3$, in the case that n=0, may additionally be S, O or $NR^1$;
$R^1$ is independently unsubstituted or substituted alkyl, unsubstituted or substituted cycloalkyl, unsubstituted or substituted heterocycloalkyl, unsubstituted or substituted aryl, unsubstituted or substituted heteroaryl, unsubstituted or substituted alkenyl, unsubstituted or substituted cycloalkenyl, unsubstituted or substituted alkynyl, $SiR^2_3$, halogen, a substituent with donor or acceptor action, where, in the case that $R^1$ is bonded to a nitrogen atom, $R^1$ is independently unsubstituted or substituted alkyl or unsubstituted or substituted aryl or unsubstituted or substituted heteroaryl, where any two $R^1$ radicals together may additionally form an alkylene or arylene bridge;
$R^2$ is independently unsubstituted or substituted alkyl or unsubstituted or substituted aryl or unsubstituted or substituted heteroaryl;
m, n are each independently 0 or 1, where the $Z^4$ and $Y^5$ groups are absent when, respectively, n and m=0;
wherein the metal complex comprises at least one deuterium atom.

According to the present invention, the ligand of the formula (I) and/or one or more further ligands which may be present in the inventive metal complex may have at least one deuterium atom. In a preferred embodiment, the ligand of the formula (I) comprises at least one deuterium atom. The at least one deuterium atom may be present in one or more of the $R^1$ and/or $R^2$ radicals, and/or at least one of the $X^4, X^5, Y^4, Y^5, Y^6, Z^1, Z^2, Z^3, Z^4$ groups is CD. More preferably, at least one of the $X^4, X^5, Y^4, Y^5, Y^6, Z^1, Z^2, Z^3, Z^4$ groups is CD.

It has been found that it is possible to provide metal complexes suitable for use in OLEDs, the OLEDs being notable for a balanced spectrum of properties, for example for good efficiencies, an outstanding lifetime and very good stabilities in the device, and also good charge transport properties and thermal stability as compared with OLEDs known in the prior art. More particularly, when the inventive metal complexes are used, it is possible to provide OLEDs which emit light in the blue region of the electromagnetic spectrum.

The inventive metal complexes can be used in any layer of an OLED, the ligand skeleton or central metal being variable to adapt to desired properties of the metal complexes. For example, it is possible to use the inventive metal complexes in the light-emitting layer, a blocking layer for electrons, a blocking layer for excitons, a blocking layer for holes, a hole transport layer and/or an electron transport layer of the OLED, depending on the substitution pattern of the inventive metal complexes and the electronic properties in further layers present in the OLED. Preference is given to using the inventive metal complexes in the light-emitting layer. In this layer, the inventive metal complexes can be used as emitter materials and/or matrix materials. Preference is given to using the inventive metal complexes as emitter materials in OLEDs.

In the context of the present invention, the terms unsubstituted or substituted aryl radical or group, unsubstituted or substituted heteroaryl radical or group, unsubstituted or substituted alkyl radical or group, unsubstituted or substituted cycloalkyl radical or group, unsubstituted or substituted heterocycloalkyl radical or group, unsubstituted or substituted alkenyl radical or group, unsubstituted or substituted alkynyl radical or group, aryl radical or group, and groups with donor and/or acceptor action are each defined as follows:

An aryl radical (or group) is understood to mean a radical which has a base skeleton of from 6 to 30 carbon atoms, preferably from 6 to 18 carbon atoms, and which is formed from an aromatic ring or a plurality of fused aromatic rings. Suitable base skeletons are, for example, phenyl, naphthyl, anthracenyl or phenanthrenyl. This base skeleton may be unsubstituted (i.e. all carbon atoms which are substitutable bear hydrogen atoms) or be substituted at one, more than one or all substitutable positions of the base skeleton. Suitable substituents are, for example, deuterium, alkyl radicals, preferably alkyl radicals having from 1 to 8 carbon atoms, more preferably methyl, ethyl or i-propyl, aryl radicals, preferably $C_6$-aryl radicals, which may in turn be substituted or unsubstituted, heteroaryl radicals, preferably heteroaryl radicals which comprise at least one nitrogen atom, more preferably pyridyl radicals, alkenyl radicals, preferably alkenyl radicals which bear one double bond, more preferably alkenyl radicals with one double bond and from 1 to 8 carbon atoms, or groups with donor or acceptor action. The aforementioned alkyl radicals, aryl radicals, heteroaryl radicals, alkenyl radicals and groups with donor or acceptor action may be deuterated at one or more positions. Suitable groups with donor or acceptor action are specified below. Most preferably, the substituted aryl radicals bear substituents selected from the group consisting of deuterium, methyl, isopropyl, F, CN, aryloxy and alkoxy, thioaryl, thioalkyl, heteroaryl. The aryl radical or the aryl group is preferably a $C_6$-$C_{18}$-aryl radical, more preferably a $C_6$-aryl radical, which is optionally substituted by at least one or more than one of the aforementioned substituents. More preferably, the $C_6$-$C_{18}$-aryl radical, preferably $C_6$-aryl radical, has none, one, two, three or four of the aforementioned substituents.

A heteroaryl radical or a heteroaryl group is understood to mean radicals which differ from the aforementioned aryl radicals in that, in the base skeleton of the aryl radicals, at least one carbon atom is replaced by a heteroatom. Preferred heteroatoms are N, O and S. Most preferably, one or two carbon atoms of the base skeleton of the aryl radicals are replaced by heteroatoms. Especially preferably, the base skeleton is selected from systems such as pyridine and five-membered heteroaromatics such as pyrrole, furan, pyrazole, imidazole, thiophene, oxazole, thiazole, triazole. The base skeleton may be substituted at one, more than one or all substitutable positions of the base skeleton. Suitable substituents are the same as have already been specified for the aryl groups.

An alkyl radical or an alkyl group is understood to mean a radical having from 1 to 20 carbon atoms, preferably from 1 to 10 carbon atoms, more preferably from 1 to 8 and most preferably from 1 to 4 carbon atoms. This alkyl radical may be branched or unbranched and may optionally be interrupted by one or more heteroatoms, preferably Si, N, O or S, more preferably N, O or S. In addition, this alkyl radical may be substituted by one or more of the substituents specified for the aryl groups. It is likewise possible that the alkyl radical bears one or more (hetero)aryl groups. In the context of the present application, for example, benzyl radicals are thus substituted alkyl radicals. All of the above-listed (hetero)aryl groups are suitable. The alkyl radicals are more preferably selected from the group consisting of methyl, ethyl, isopropyl, n-propyl, n-butyl, isobutyl and tert-butyl; very particular preference is given to methyl, isopropyl, and the corresponding partially or completely deuterated derivatives, for example $CD_3$, $-C(CD_3)_2D$ or $-C(CD_3)_3$.

A cycloalkyl radical or a cycloalkyl group is understood to mean a radical having from 3 to 20 carbon atoms, preferably from 3 to 10 carbon atoms, more preferably from 3 to 8 carbon atoms. This base skeleton may be unsubstituted (i.e. all carbon atoms which are substitutable bear hydrogen atoms) or may be substituted at one, more than one or all substitutable positions of the base skeleton. Suitable substituents are the groups already specified above for the aryl radicals. Examples of suitable cycloalkyl radicals are cyclopropyl, cyclopentyl and cyclohexyl.

A heterocycloalkyl radical or a heterocycloalkyl group are understood to mean radicals which differ from the aforementioned cycloalkyl radicals in that, in the base skeleton of the cycloalkyl radicals, at least one carbon atom is replaced by a heteroatom. Preferred heteroatoms are N, O and S. Most preferably, one or two carbon atoms of the base skeleton of the cycloalkyl radicals are replaced by heteroatoms. Examples of suitable heterocycloalkyl radicals are radicals derived from pyrrolidine, piperidine, piperazine, tetrahydrofuran, dioxane.

An alkenyl radical or an alkenyl group is understood to mean a radical which corresponds to the aforementioned alkyl radicals having at least two carbon atoms, with the difference that at least one C—C single bond of the alkyl radical is replaced by a C—C double bond. The alkenyl radical preferably has one or two double bonds.

An alkynyl radical or an alkynyl group is understood to mean a radical which corresponds to the aforementioned alkyl radicals having at least two carbon atoms, with the difference that at least one C—C single bond of the alkyl radical is replaced by a C—C triple bond. The alkynyl radical preferably has one or two triple bonds.

In the context of the present application, the terms alkylene and arylene are each as defined for the alkyl and aryl radicals, with the difference that the alkylene and arylene groups have two bonding sites.

Preferred alkylene groups are $(CR^4_2)_n$, where $R^4$ is deuterium, H or alkyl, preferably deuterium, H, methyl or ethyl, more preferably H or D, and n is from 1 to 3, preferably 1 or 2, more preferably 1. The alkylene group is most preferably $CH_2$ or $CD_2$.

Preferred arylene groups are 1,2-, 1,3- or 1,4-phenylene groups which are unsubstituted or which may bear the substituents specified for the aryl radicals.

In the context of the present application, a group or a substituent with donor or acceptor action is understood to mean the following groups:

groups with donor action are understood to mean groups which have a+I and/or +M effect, and groups with acceptor action to mean groups which have a–I and/or –M effect. Suitable groups with donor or acceptor action are halogen radicals, preferably F, Cl, Br, more preferably F, alkoxy radicals or aryloxy radicals, $OR^2$, carbonyl radicals, ester radicals, both oxycarbonyl and carbonyloxy, amino groups, $NR_2^2$, amide radicals, $CH_2F$ groups, $CHF_2$ groups, $CF_3$ groups, CN groups, thio groups, sulfonic acid groups, sulfonic ester groups, boronic acid groups, boronic ester groups, phosphonic acid groups, phosphonic ester groups, phosphine radicals, sulfoxide radicals, sulfonyl radicals, sulfide radicals, $SR^2$, nitro groups, OCN, boran radicals, silyl groups, $SiR_3^2$, stannate radicals, imino groups, hydrazine radicals, hydrazone radicals, oxime radicals, nitroso groups, diazo groups, phosphine oxide groups, hydroxyl groups or SCN groups. Very particular preference is given to F, Cl, CN, aryloxy, alkoxy, amino, $CF_3$ groups, sulfonyl, silyl, sulfide and heteroaryl. Very especially preferred are heteroaryl, silyl $(SiR_3^2)$, F, alkoxy or aryloxy $(OR^2)$, sulfide radicals $(SR^2)$, amino $(NR_2^2)$ and CN. The $R^2$ radicals are defined below.

The aforementioned groups with donor or acceptor action do not rule out the possibility that further radicals and substituents which are specified in the present application and are not listed in the above list of groups with donor or acceptor action have donor or acceptor action.

The aryl radicals or groups, heteroaryl radicals or groups, alkyl radicals or groups, cycloalkyl radicals or groups, heterocycloalkyl radicals or groups, alkenyl radicals or groups, alkynyl radicals or groups and groups with donor and/or acceptor action, and also the alkylene and arylene radicals or groups, may—as mentioned above—be substituted or unsubstituted. In the context of the present application, an unsubstituted group is understood to mean a group in which the substitutable atoms of the group bear hydrogen atoms. In the context of the present application, a substituted group is understood to mean a group in which one or more substitutable atom(s) bear a substituent instead of a hydrogen atom at least in one position. Suitable substituents are the substituents specified above for the aryl radicals or groups.

When radicals with the same numbering occur more than once in the compounds according to the present application, these radicals may each independently be defined as specified.

In a preferred embodiment, at least one of the $X^1$ and $Y^1$ groups in the ligand of the formula (I) is N, preference being given to exactly one of the $X^1$ or $Y^1$ groups being N, particular preference to $X^1$ being N.

The symbols $X^1, X^2, X^3, X^4, X^5, Y^1, Y^2, Y^3, Y^4, Y^5, Y^6, Z^1, Z^2, Z^3, Z^4$ are each dependently defined as follows:

$Y^5, Z^4$
are each independently CD, $CR^1$, CH or N;

$X^1, X^2, X^3, Y^1, Y^2, Y^3$
are each independently N or C;

$X^4, X^5$
are each independently CD, $CR^1$, CH, N, S or O; where $X^4$ or $X^5$ may additionally be $NR^1$ when the other $X^5$ or $X^4$ radical in each case is N, CH, CD or $CR^1$;

$Y^4, Y^6$ are each independently CD, $CR^1$, CH, N; where $Y^4$ or $Y^6$, in the case that m=0, may additionally be S, O or $NR^1$;

$Z^1, Z^2, Z^3$ are each independently CD, $CR^1$, CH, N; where $Z^1, Z^2$ or $Z^3$, in the case that n=0, may additionally be S, O or $NR^1$.

In a preferred embodiment, at least one of the $X^4, X^5, Y^4, Y^5, Y^6, Z^1, Z^2, Z^3, Z^4$ groups comprises at least one deuterium atom. More preferably, at least one of the $X^4, X^5, Y^4, Y^5, Y^6, Z^1, Z^2, Z^3, Z^4$ groups is CD.

Preferably, 0, 1, 2 of the aforementioned $X^4, X^5, Y^4, Y^6, Z^1, Z^2$ and $Z^3$ groups, more preferably $X^4, Y^4, Y^6, Z^1, Z^2$ and $Z^3$, are each S or O, where, for example, $Y^4$ and/or $Z^1$ in the ligands of the general formula (I) is S or O and the remaining groups are each as defined above, but are not S or O.

In a particularly preferred embodiment, the present invention relates to a metal complex in which the $X^1$ group is N and the remaining aforementioned groups are each as defined above.

Most preferably, the symbols $X^1, X^2, X^3, X^4, X^5, Y^1, Y^2, Y^3, Y^4, Y^5, Y^6, Z^1, Z^2, Z^3, Z^4$ are each independently defined as follows:

$X^2, Y^1, Y^2, Y^3$
are each C;
$X^1$
is N;
$X^3$
is C or N, preferably N;
$X^5$
is N, CD or $CR^1$; preferably CD;
$X^4$
is $CR^1$, CD, $NR^1$, O or S, preferably $CR^1$ or CD;
$Y^4, Y^5, Y^6$
are each independently CH, CD or $CR^1$, preferably CD;
$Z^1, Z^2, Z^3, Z^4$
are each independently CH, CD, $CR^1$ or N, where $Z^1, Z^2$ or $Z^3$, in the case that n=0, may additionally be S, O or $NR^1$; preferably, $Z^1, Z^2$ and $Z^4$ are each CD and $Z^3$ is $CR^1$.

Additionally preferably, $X^1$ is N and $X^4$ and/or $X^5$ is CD, where the remaining aforementioned groups are each as defined above. Most preferably, $X^1$ and $X^3$ are each N, where $X^5$ is preferably additionally CD or $CR^1$ and $X^4$ is $CR^1$. The remaining aforementioned groups are each as defined above. Very especially preferably, $X^1$ and $X^3$ are each N, $X^4$ and $Z^3$ are each $CR^1$, and $X^5, Y^4, Y^5, Y^6, Z^1, Z^2$ and $Z^4$ are each CD, where the remaining aforementioned groups are each as defined above. Most preferably, the remaining aforementioned groups in the latter case are each defined as deuterium or $R^1$, where $R^1$ may be as defined below.

In the ligands of the general formula (I), $R^1$ is independently unsubstituted or substituted alkyl, unsubstituted or substituted cycloalkyl, unsubstituted or substituted heterocycloalkyl, unsubstituted or substituted aryl, unsubstituted or substituted heteroaryl, unsubstituted or substituted alkenyl, unsubstituted or substituted cycloalkenyl, unsubstituted or substituted alkynyl, $SiR^2_3$, halogen, a substituent with donor or acceptor action, where, in the case that $R^1$ is bonded to a nitrogen atom, $R^1$ is independently unsubstituted or substituted alkyl or unsubstituted or substituted aryl or unsubstituted or substituted heteroaryl, or any two $R^1$ radicals together may form an alkylene or arylene bridge. The two $R^1$ radicals may belong to a single cycle of the ligands of the general formula (I) or to two different cycles of the ligand of the general formula (I). For example, in the case when $X^4$ and $X^5$ are each $CR^1$, the two $R^1$ radicals together may form an alkylene or arylene bridge. It is likewise possible that, in the case when $Z^1$ and $X^4$, or $Z^4$ (when n=1) or $Z^3$ (when n=0) and $Y^4$, are $CR^1$, two $R^1$ radicals together form an alkylene or arylene bridge. Suitable and preferred alkyl, cycloalkyl, heterocycloalkyl, aryl, heteroaryl, alkenyl, cycloalkenyl, alkynyl groups and substituents with donor or acceptor action and alkylene and arylene groups are the aforementioned groups. $R^1$ is preferably independently unsubstituted or substituted alkyl, unsubstituted or substituted aryl, unsubstituted or substituted heteroaryl, $SiR^2_3$, halogen, preferably F, $OR^2$, $SR^2$, $NR^2_2$, $CF_3$ or CN where $R^1$, in the case that $R^1$ is bonded to a nitrogen atom, is preferably independently unsubstituted or substituted alkyl, unsubstituted or substituted aryl. Most preferably, $R^1$ is independently unsubstituted or substituted alkyl, unsubstituted or substituted aryl, unsubstituted or substituted heteroaryl or $SiR^2_3$. Additionally most preferably, $R^1$ is methyl, isopropyl, or the corresponding partially or completely deuterated derivatives thereof, for example $CD_3$, —$C(CD_3)_2D$ or —$C(CD_3)_3$; unsubstituted or substituted $C_6$-aryl, where suitable substituents are especially deuterium, methyl, isopropyl, $CD_3$, —$C(CD_3)_2D$ or —$C(CD_3)_3$, particular preference being given to ortho-disubstituted $C_6$-aryls; or $C_5$- or $C_6$-heteroaryl, e.g.

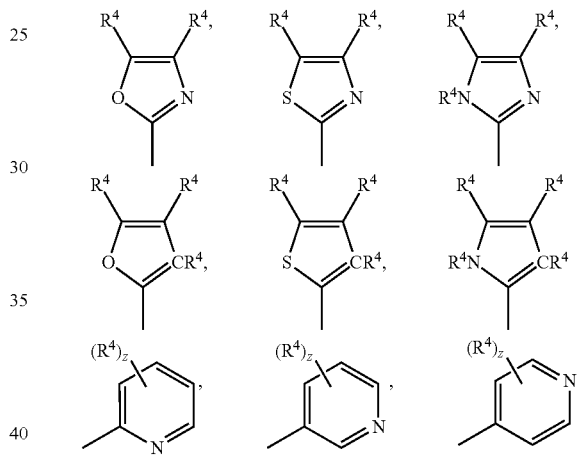

in which
$R^4$ is independently unsubstituted or substituted alkyl, unsubstituted or substituted aryl, unsubstituted or substituted heteroaryl or $SiR^2_3$, preferably hydrogen, deuterium, methyl, ethyl, n-propyl, isopropyl, n-butyl, sec-butyl, isobutyl, tert-butyl or the partially or completely deuterated derivatives thereof, for example $CD_3$, —$C(CD_3)_2D$ or —$C(CD_3)_3$; unsubstituted or substituted $C_6$-aryl or $C_5$- or $C_6$-heteroaryl, more preferably hydrogen or deuterium; and
z is 0, 1, 2, 3 or 4, preferably 0, 1 or two;
where
$R^1$, in the case that $R^1$ is bonded to a nitrogen atom, is more preferably independently methyl, ethyl, isopropyl, n-propyl, n-butyl, isobutyl, sec-butyl or tert-butyl or $C_6$-aryl which may be unsubstituted or substituted, preferably phenyl or tolyl.

$R^2$ is independently unsubstituted or substituted alkyl or unsubstituted or substituted aryl, where suitable and preferred alkyl and aryl radicals and suitable substituents are specified above. $R^2$ is preferably methyl, ethyl, isopropyl, n-propyl, n-butyl, isobutyl, sec-butyl or tert-butyl or $C_6$-aryl which may be unsubstituted or substituted, preferably phenyl or tolyl.

m and n in the ligands of the general formula (I) may each independently be 0 or 1, where the $Z^4$ and $Y^5$ groups are absent when, respectively, n and m=0. In the case that m=0, the aromatic 5-membered ring formed from the elements $X^1$, $X^2$, $X^3$, $X^4$ and $X^5$ is thus joined to a 5-membered ring formed from the elements $Y^1$, $Y^2$, $Y^3$, $Y^4$ and $Y^6$. When m=1, the aromatic 5-membered ring formed from $X^1$, $X^2$, $X^3$, $X^4$ and $X^5$ is joined to an aromatic 6-membered ring formed from the elements $Y^1$, $Y^2$, $Y^3$, $Y^4$, $Y^5$ and $Y^6$. When n=0, the aromatic 5-membered ring formed from $X^1$, $X^2$, $X^3$, $X^4$, $X^5$ is joined to an aromatic 5-membered ring formed from $Z^1$, $Z^2$, $Z^3$ and two carbon atoms, and, when n=1, the aromatic 5-membered ring formed from $X^1$, $X^2$, $X^3$, $X^4$ and $X^5$ is joined to an aromatic 6-membered ring formed from $Z^1$, $Z^2$, $Z^3$, $Z^4$ and two carbon atoms. Preferably, m=1. In a further preferred embodiment, n=1. More preferably, both n and m=1.

The inventive metal complex preferably comprises a metal atom selected from the group consisting of transition metals of group IB, IIB, IIIB, IVB, VB, VIB, VIIB, VIII of the Periodic Table of the Elements (CAS version), in any oxidation state possible for the particular metal atom. The inventive metal complexes preferably comprise a metal atom M selected from the group consisting of Ir, Co, Rh, Ni, Pd, Pt, Fe, Ru, Os, Cr, Mo, W, Mn, Tc, Re, Ag, Au and Cu more preferably Ir, Os, Ru, Rh, Pd, Co, Ni and Pt, most preferably Ir, Pt, Rh, Ru and Os, in any oxidation state possible for the particular metal atom. Especially preferably, Pt(II), Pt(IV), Ir(I), Ir(III), Os(II) and Ru(II) are used, even more especially preferably Pt(II), Ir(III) and Os(II), and most preferably Ir(III).

As well as the at least one ligand of the general formula (I), the inventive metal complex may comprise further ligands other than the ligand of the general formula (I). For example, as well as at least one ligand of the general formula (I), one or more uncharged mono- or bidentate ligands K and if appropriate one or more mono- or dianionic ligands J, which may be mono- or bidentate, may be present. In addition, different ligands of the formula (I) may be present in the inventive metal complex. A bidentate ligand is understood to mean a ligand which is coordinated to the metal atom M at two sites.

A monodentate ligand is understood to mean a ligand which coordinates to the metal atom M at one site on the ligand.

The present invention thus relates, in a preferred embodiment, to metal complexes of the general formula (II)

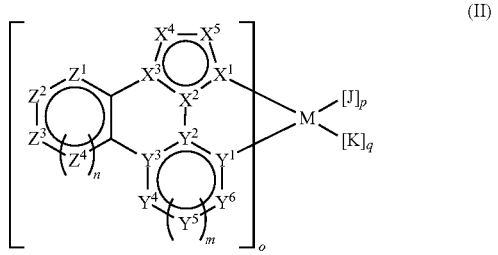

(II)

in which

M is a metal atom selected from the group consisting of transition metals of groups IB, IIB, IIIB, IVB, VB, VIB, VIIB, VIII of the Periodic Table of the Elements (CAS version), in any oxidation state possible for the particular metal atom; preferably Ir(III), Pt(II) or Os(II), more preferably Ir(III);

J is a mono- or dianionic ligand which may be mono- or bidentate, preferably a bidentate monoanionic ligand;

K is an uncharged, mono- or bidentate ligand which is generally not photoactive: preferred ligands K are phosphines, especially trialkylphosphines, e.g. $PEt_3$, $PnBu_3$, triarylphosphines, e.g. $PPh_3$; phosphonates and derivatives thereof, arsenates and derivatives thereof, phosphites, CO, nitriles, amines, dienes which can form a $\pi$-complex with M, for example 2,4-hexadiene, $\eta^4$-cyclooctadiene and $\eta^2$-cyclooctadiene (in each case 1,3 and 1,5), allyl, methallyl, cyclooctene, norbornadiene and uncharged biscarbenes, for example the uncharged bicarbenes disclosed in WO 2008/000726;

o is 1, 2, 3 or 4; where o is 1, 2 or 3 when M=Ir(III), preferably 2 or 3; and is 1 or 2 when M=Pt(II) or Os(II);

p is 0, 1, 2, 3 or 4; where p is 0, 1, 2, 3 or 4 when M=Ir(III), preferably 0 or 2; and is 0, 1 or 2 when M=Pt(II) and Os(II), preferably 0 or 2, where p is the number of bonding sites to the metal M, i.e., when p=2, the ligands may be two monodentate ligands or one bidentate ligand;

q is 0, 1, 2, 3 or 4; where q is 0, 1 or 2 when M=Ir(III), preferably 0; is 0 or 1 when M=Pt(II), preferably 0; and is 2 or 3 for Os(II), preferably 2, where q is the number of bonding sites to the metal M, i.e., when q=2, the ligands may be two monodentate ligands or one bidentate ligand;

where o, p and q depend on the oxidation state and coordination number of the metal atom used and on the charge of the ligands.

Both the ligand J and the ligand K may have one or more deuterium atoms.

In the case that the number o, p or q is >1, the ligands of the formula (I), K or J used may each be the same or different.

When M=Ir(III), the sum of o, p+q in the inventive metal complexes of the formula (II) is generally 3, 4 or 5, i.e., in the case when 3 ligands of the formula I are present, o is 3, and when 2 ligands of the formula I and, for example, 1 bidentate monoanionic ligand J are present, o is 2 and p is 2. When M=Pt(II) the sum of o+p is generally 2 or 3, i.e., in the case when 2 ligands of the formula I are present, o is 2, and, when 1 ligand of the formula I and, for example, 1 bidentate monoanionic ligand J are present, o is 1 and p is 2, where o is in each case at least 1. For Os(II), the sum of o, p+q in the inventive metal complexes of the formula (II) is generally 4 or 5, i.e., when 2 ligands of the formula (I) and, for example, 1 bidentate uncharged ligand K are present, o is 2 and q is 2, and, in the case when, for example, 1 ligand of the formula (I), 1 bidentate monoanionic ligand J and 1 uncharged bidentate ligand K are present, o is 1, p is 2 and q is 2.

The symbols $X^1$, $X^2$, $X^3$, $X^4$, $X^5$, $Y^1$, $Y^2$, $Y^3$, $Y^4$, $Y^5$, $Y^6$, $Z^1$, $Z^2$, $Z^3$, $Z^4$, m and n in the metal complex of the formula (II) are each defined as specified.

If different isomers of the inventive metal complexes may be present, the present invention comprises both the individual isomers of the metal complexes in each case and mixtures of different isomers in any desired mixing ratio. In general, different isomers of the metal complexes can be separated by processes known to those skilled in the art, for example by chromatography, sublimation or crystallization.

Typically, the bidentate monoanionic ligands J used are nonphotoactive or photoactive (for example heteroleptic complexes with carbenes, phenylpyridines or phenylimidazoles) ligands. Suitable ligands J are, for example, bidentate monoanionic ligands of the general formula

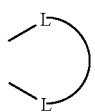

in which L is in each case independently selected from O, N and C. Preference is given to bidentate monoanionic ligands J in which both L groups are O, C or N, or one L groups is O and the other L group is N or C, or one L group is C and the other L group is N. Particularly preferred bidentate monoanionic ligands are acetylacetonate and derivatives thereof, picolinate and derivatives thereof, bidentate monoanionic carbene ligands and derivatives thereof, for example carbene ligands which are specified in WO 2005/019373, WO 2005/0113704, WO 2006/018292, WO 2006/056418, WO 2007/115981, WO 2007/115970, WO 2008/000727, WO 2006/067074, WO 2006/106842, WO 2007/018067, WO 2007/058255, WO 2007/069542, US 2007/108891, WO 2007/058080, WO 2007/058104, and also the bidentate monoanionic ligands specified in WO 02/15645, WO 2005/123873, US 2007/196690, WO 2006/121811. The bidentate monoanionic ligands are more preferably selected from the group consisting of acetylacetonate, picolinate, carbenes such as N-methyl-N-arylimidazole carbene, arylpyridines such as 2-arylpyridines, especially phenylpyridines such as 2-phenylpyridine, arylimidazoles such as 2-arylimidazoles, especially phenylimidazoles, such as 2-phenylimidazole, and derivatives of the aforementioned compounds. In the aforementioned bidentate monoanionic ligands, one or more hydrogen atoms of the ligands may be replaced by deuterium.

In a particularly preferred embodiment, the inventive metal complex has the general formula (IIa)

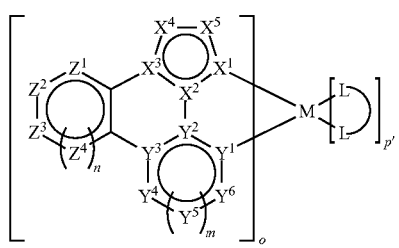
(IIa)

in which:

M is a metal atom selected from the group consisting of transition metals of groups IB, IIB, IIIB, IVB, VB, VIB, VIIB, VIII of the Periodic Table of the Elements (CAS version), in any oxidation state possible for the particular metal atom; preferably Ir(III), Pt(II), more preferably Ir(III);

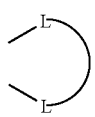

is a bidentate monoanionic ligand which may have one or more deuterium atoms; L in the bidentate monoanionic ligand is preferably in each case independently selected from O, N and C; particular preference is given to bidentate monoanionic ligands in which both L groups are O, C or N or one L group is O and the other L group is N or C or one L group is C and the other L group is N; the bidentate monoanionic ligands are even more preferably selected from the group consisting of acetylacetonate, picolinate, carbenes such as N-methyl-N-arylimidazolecarbene, arylpyridines such as 2-arylpyridines, especially phenylpyridines such as 2-phenylpyridine, and arylimidazoles such as 2-arylimidazoles, especially phenylimidazoles such as 2-phenylimidazole, and derivatives of the aforementioned compounds o is 1, 2, 3 or 4; where o is 1, 2 or 3 when M=Ir(III), preferably 2 or 3; and is 1 or 2 when M=Pt(II);

p' is 0, 1 or 2; where p' is 0, 1 or 2 when M=Ir(III), preferably 0 or 1; and is 0 or 1 when M=Pt(II); where p' is the number of ligands

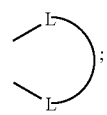

where o and p' depend on the oxidation state and coordination number of the metal atom used.

When M=Ir(III), the sum of o+p' in the inventive metal complexes of the formula (IIa) is generally 3, and, when M=Pt(II), the sum of o+p' is generally 2, where o is in each case at least 1.

The symbols $X^1, X^2, X^3, X^4, X^5, Y^1, Y^2, Y^3, Y^4, Y^5, Y^6, Z^1, Z^2, Z^3, Z^4$, m and n in the metal complex of the formula (II) are each as defined above. In addition, further embodiments of M of the bidentate monoanionic ligand and of o and p' are the embodiments specified above for M, the bidentate monoanionic ligand, o and p' (or p, where p'=1 corresponds to p=2).

In a particularly preferred embodiment, the present invention relates to metal complexes of the formula (IIaa)

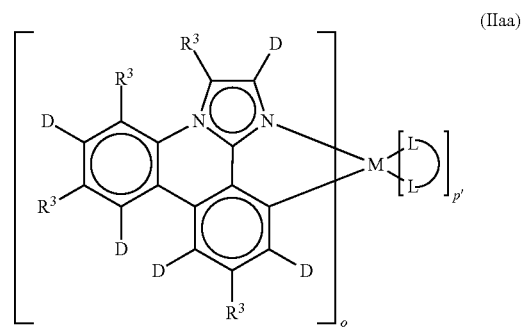
(IIaa)

in which M, o and p' are each independently as defined above;

D is deuterium, and $R^3$ is independently deuterium or $R^1$.

Suitable embodiments for $R^1$ are as defined above.

Preferred inventive metal complexes of the formula (IIaa) are listed below by way of example.

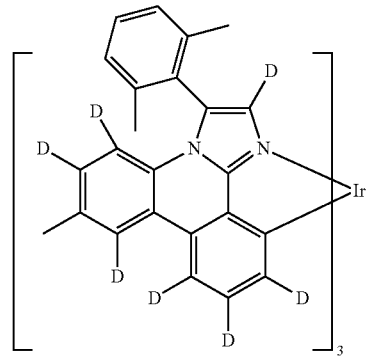
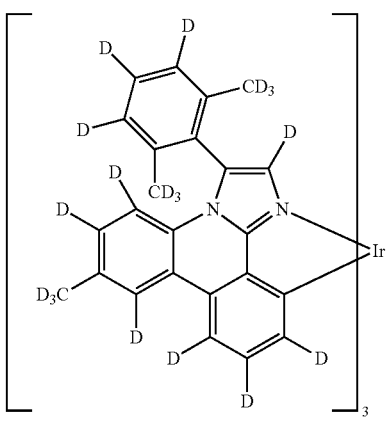
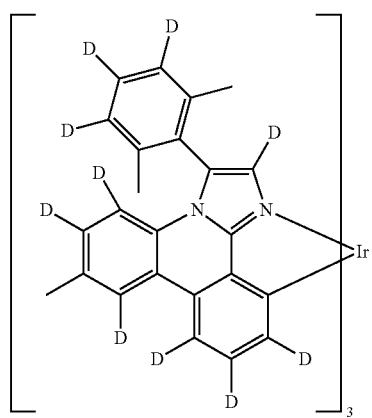
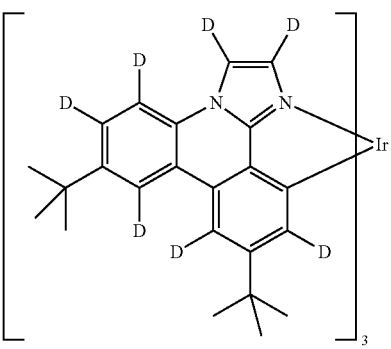
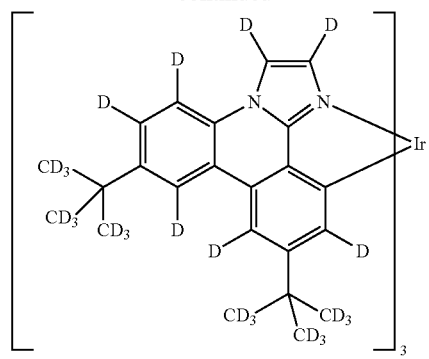
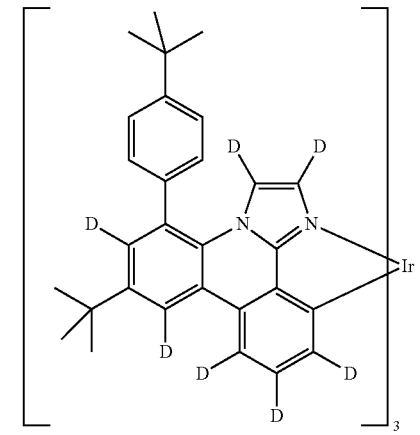
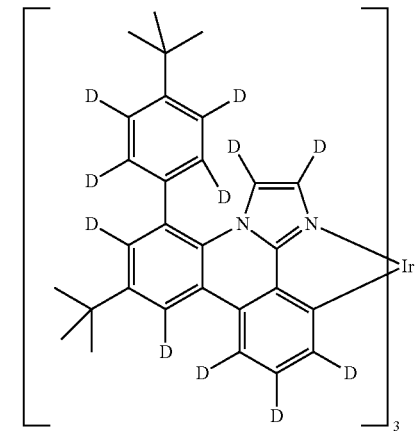
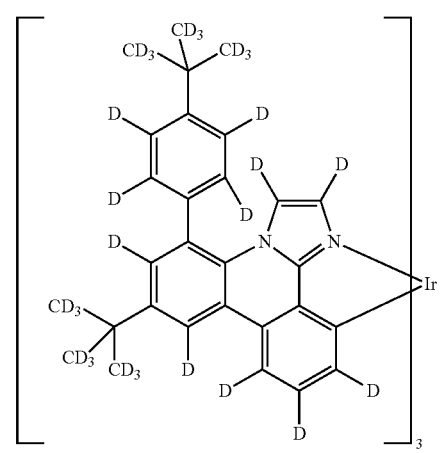

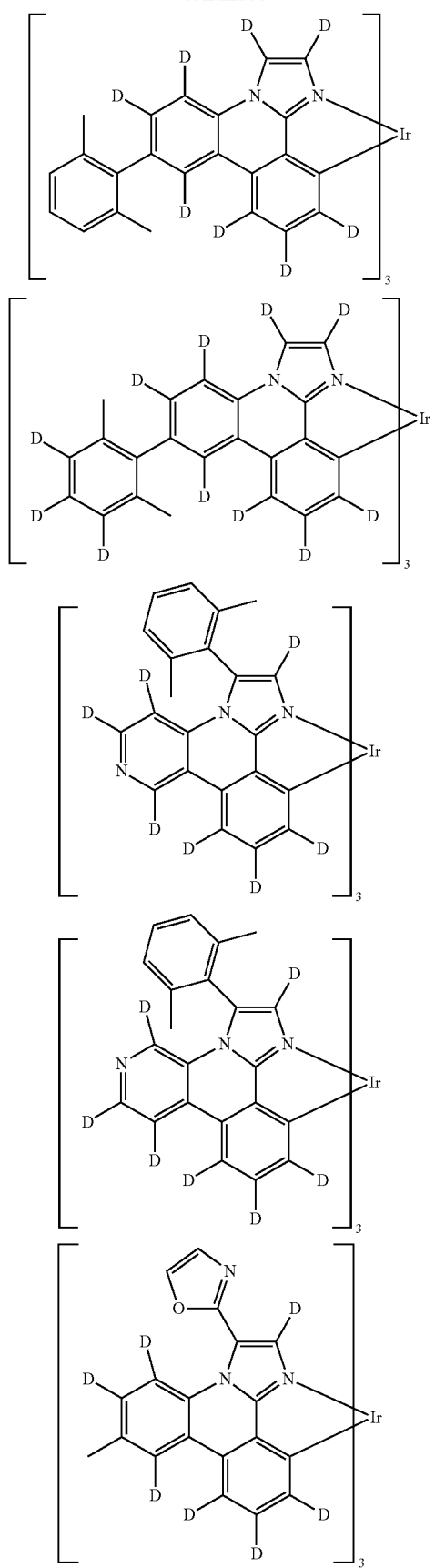
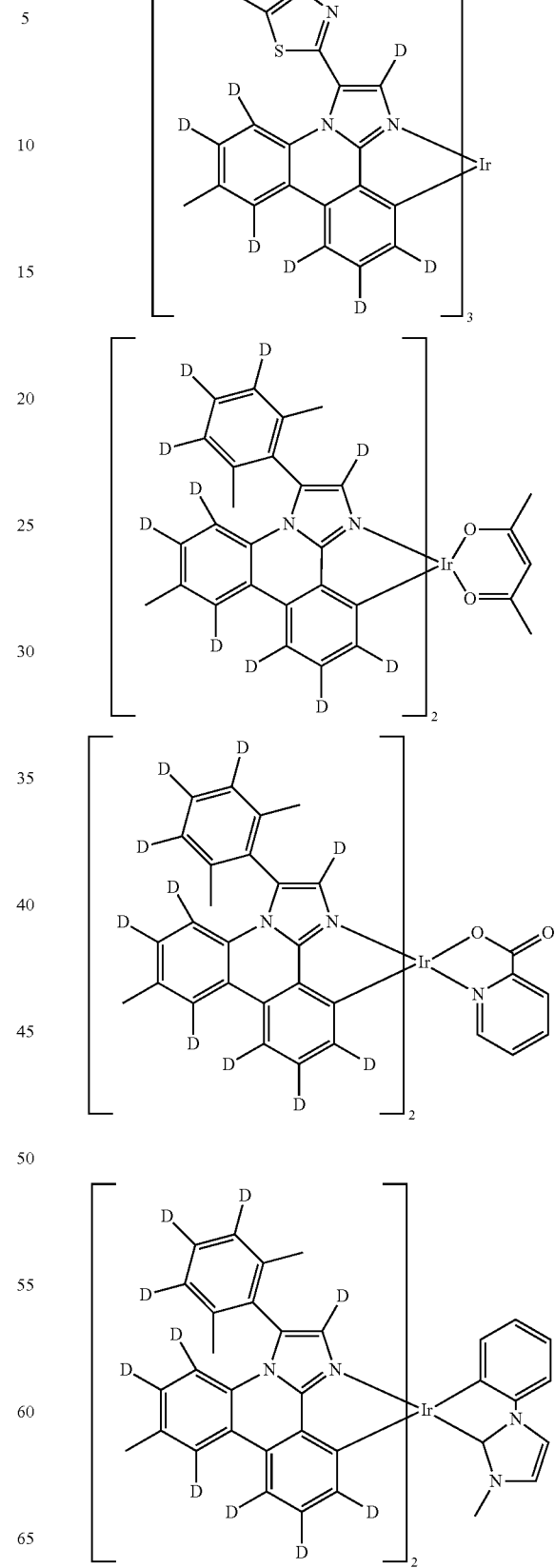

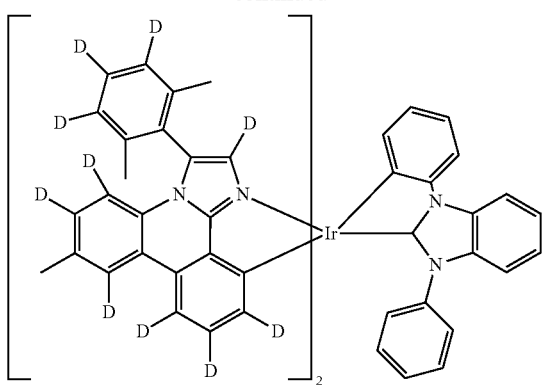
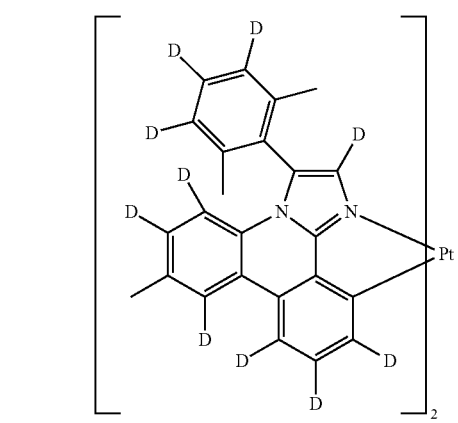
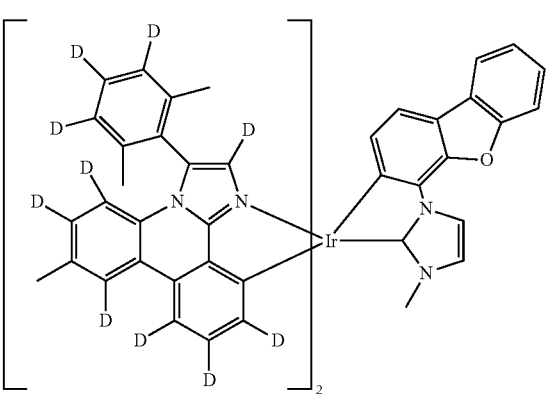
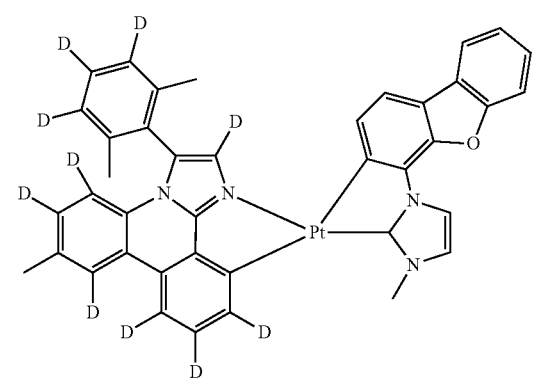
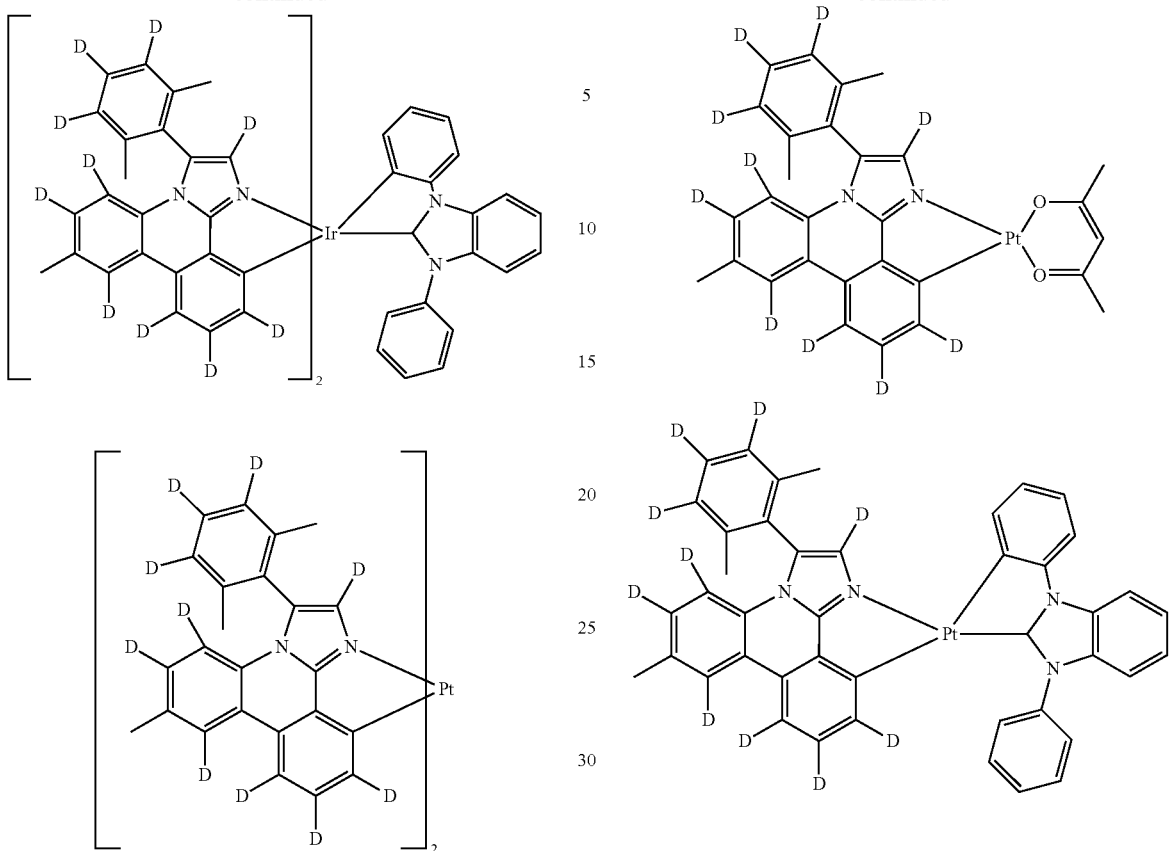
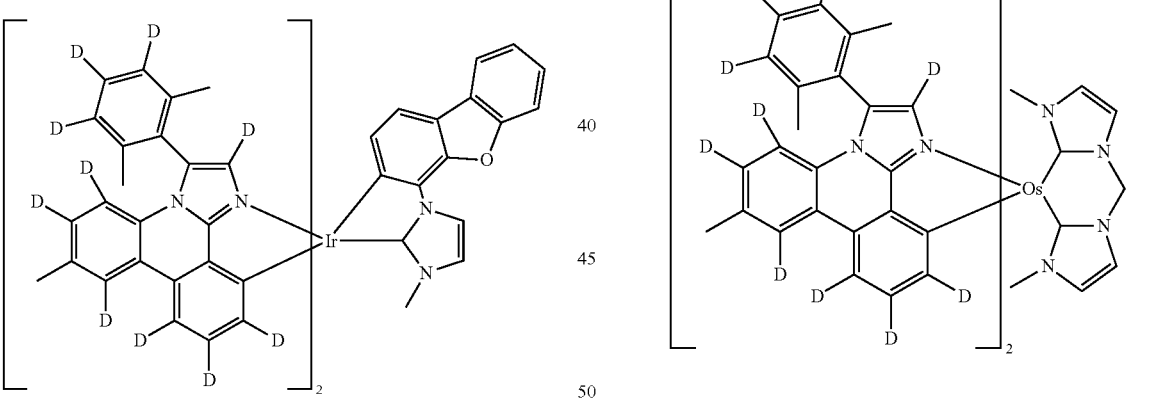
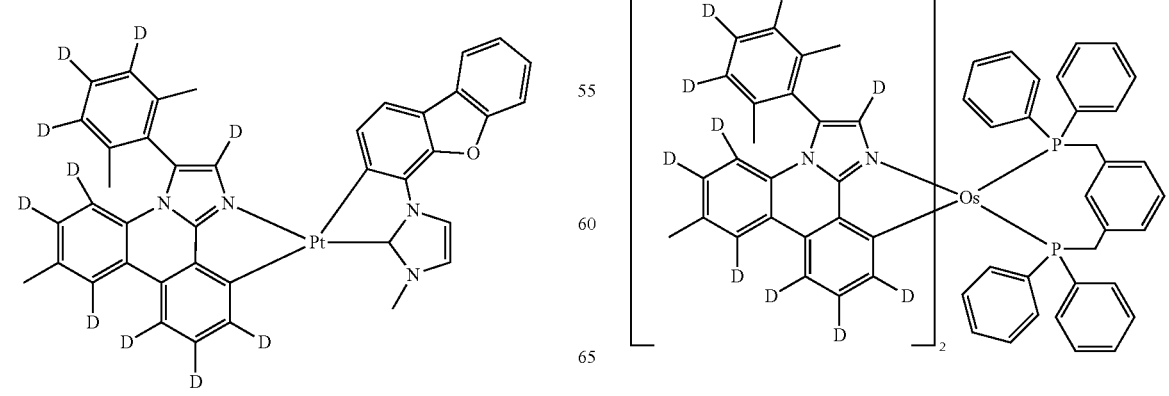

Further examples of preferred inventive metal complexes are specified below:
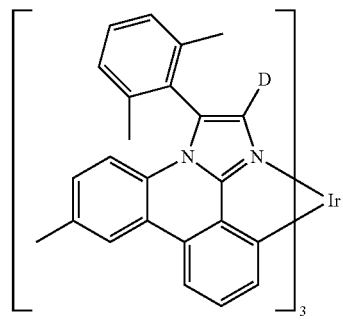
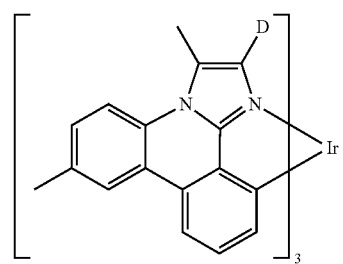
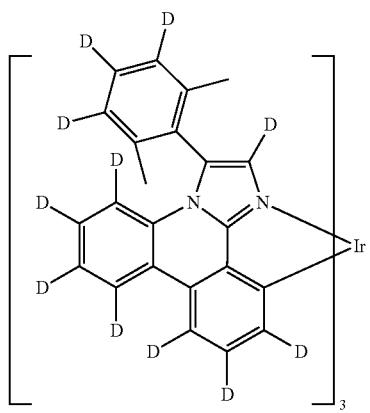
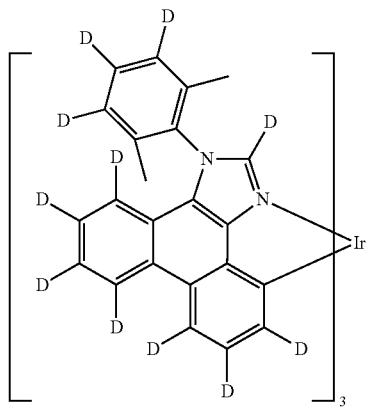
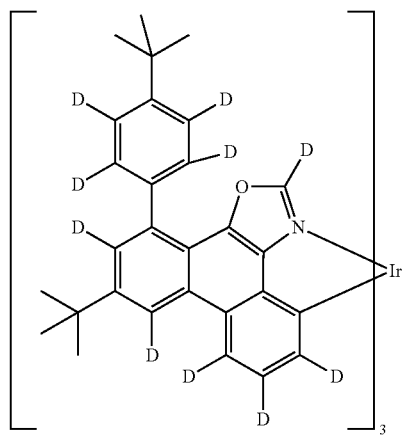
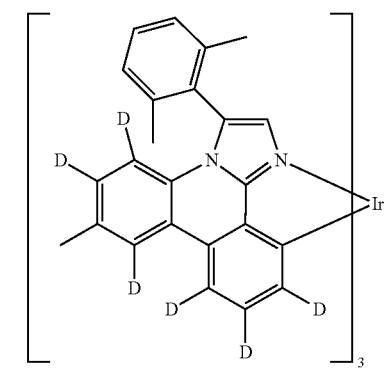
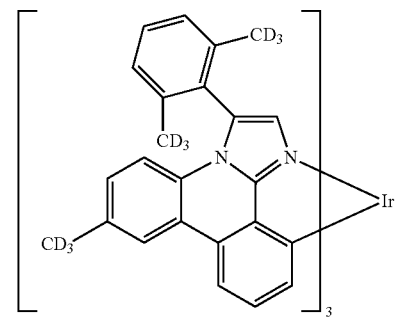
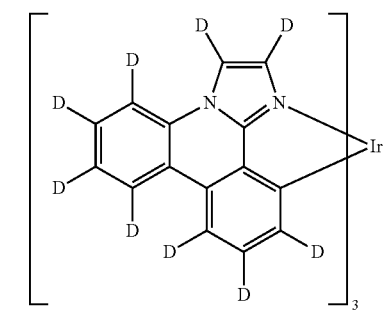
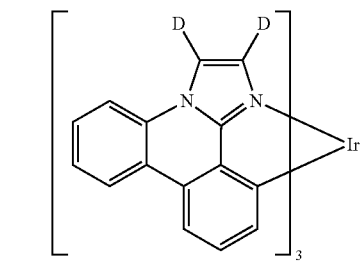

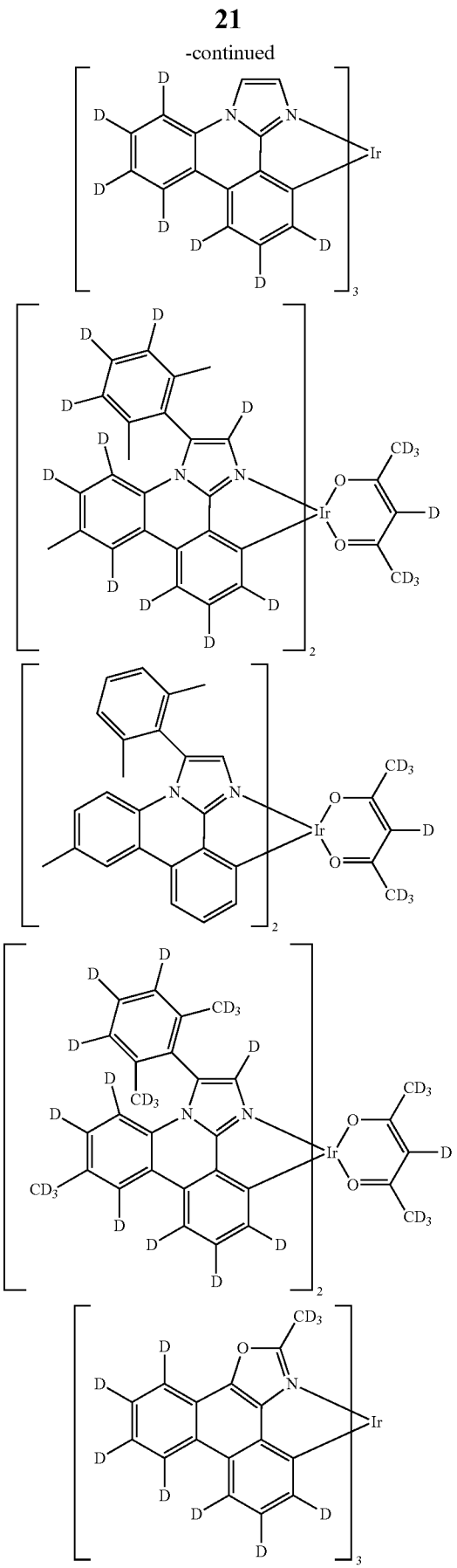

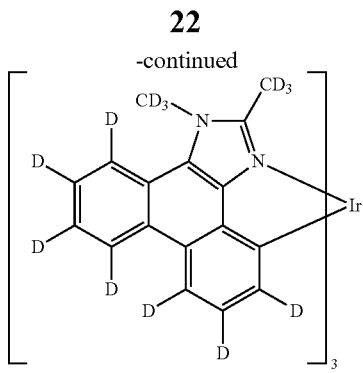

The inventive metal complexes can be prepared by processes known to those skilled in the art or analogously to processes known to those skilled in the art. Suitable preparation processes are, for example, analogous to processes specified in the examples of WO 2007/095118, where the preparation of the inventive metal complexes additionally comprises the step of introducing at least one deuterium atom into the metal complex. Deuterium atoms are introduced into the ligand of the formula (I) of the inventive metal complex by processes known to those skilled in the art. Suitable processes for exchanging hydrogen atoms for deuterium atoms are specified, for example, in the review article J. Atzrodt, V. Derdau, T. Fey, J. Zimmermann, *Angew. Chem. Int. Ed.* 2007, 46, 7744-7765.

Typically, the inventive metal complexes are prepared proceeding from the ligand precursors corresponding to the ligands of the general formula (I). The inventive metal complexes are prepared by reacting at least one ligand precursor based on the ligands of the general formula (I) with a metal complex comprising at least one metal M, where M is as defined above.

The molar ratio between the ligand precursors based on the ligands of the formula (I) and the metal complex comprising at least one metal M depends on the structure of the desired inventive metal complex and on the number of ligands of the formula (I). In the case that o in the inventive metal complexes is >1, it is possible that these metal complexes are obtained by reacting the metal complex comprising at least one metal M with identical ligand precursors or by reacting it with different ligand precursors. Suitable processes and reaction sequences for the preparation of the different inventive metal complexes are known to those skilled in the art.

The metal complex which comprises at least one metal M and is to be reacted with the ligand precursor is a metal complex comprising at least one metal atom selected from the group consisting of transition metals of group IIB, IIIB, IVB, VB, VIB, VIIB, VIII of the Periodic Table of the Elements (CAS version) and Cu, preferably selected from the group consisting of Ir, Co, Rh, Ni, Pd, Pt, Fe, Ru, Os, Cr, Mo, W, Mn, Tc, Re and Cu, more preferably Ir, Os, Ru, Rh, Pd, Co and Pt, most preferably Ir, Pt, Rh, Pd, Ru and Os in any suitable oxidation state possible for the particular metal.

Suitable metal complexes to be reacted with the ligand precursor are known to those skilled in the art. Examples of suitable metal complexes are: $Pd(OAc)_2$, $Pt(cod)Cl_2$, $Pt(cod)Me_2$, $Pt(acac)_2$, $Pt(PPh_3)_2Cl_2$, $PtCl_2$, $[Rh(cod)Cl]_2$, $Rh(acac)CO(PPh_3)$, $Rh(acac)(CO)_2$, $Rh(cod)_2BF_4$, $RhCl(PPh_3)_3$, $RhCl_3 \cdot nH_2O$, $Rh(acac)_3$, $[Os(CO)_3I_2]_2$, $[Os_3(CO)_{12}]$, $OsH_4(PPh_3)_3Cp_2Os$, $Cp^*_2Os$, $H_2OsCl_6 \cdot 6H_2O$, $OsCl_3 \cdot H_2O$, $Ru(acac)_3$, $RuCl_2(cod)$, $Ru(2$-methylallyl$)_2(cod)$, $[(\mu$-Cl$)Ir(\eta^4$-1,5-cod$)]_2$, $[(\mu$-Cl$)Ir(\eta^2$-coe$)_2]_2$, $Ir(acac)_3$, $IrCl_3 \cdot nH_2O$, $(tht)_3IrCl_3$, $Ir(\eta^3$-allyl$)_3$, $Ir(\eta^3$-methallyl$)_3$, in which cod is cyclooctadiene, coe is cyclooctene, acac is acetylacetonate and tht is tetrahydrothiophene. The metal complexes can be prepared by processes known to those skilled in the art or are commercially available.

After the aforementioned reaction of the metal complex to be reacted with the ligand precursor with one or more ligand precursors, the resulting inventive metal complex is generally worked up and, if appropriate, purified by processes known to those skilled in the art. Typically, workup and purification are effected by extraction, column chromatography and/or recrystallization by processes known to those skilled in the art.

The inventive metal complexes are used in organic light-emitting diodes (OLEDs). They are suitable as emitter substances, since they have an emission (electroluminescence) in the visible region of the electromagnetic spectrum. With the aid of the inventive metal complexes as emitter substances, it is possible to provide compounds which exhibit electroluminescence especially in the blue region of the electromagnetic spectrum with good efficiency. At the same time, the quantum yield is high and especially the lifetime and the stability of the inventive metal complexes in the device are high.

In addition, the inventive metal complexes are suitable as electron, exciton or hole blockers, or hole conductors, electron conductors, hole injection layer or matrix material in OLEDs, depending on the ligands used and the central metal used.

Organic light-emitting diodes (OLEDs) are in principle composed of several layers:
1. Anode (1)
2. Hole-transporting layer (2)
3. Light-emitting layer (3)
4. Electron-transporting layer (4)
5. Cathode (5)

However, it is also possible that the OLED does not have all of the layers mentioned; for example an OLED having the layers (1) (anode), (3) (light-emitting layer) and (5) (cathode) is likewise suitable, in which case the functions of the layers (2) (hole-transporting layer) and (4) (electron-transporting layer) are assumed by the adjacent layers. OLEDs which have the layers (1), (2), (3) and (5), or the layers (1), (3), (4) and (5), are likewise suitable.

The inventive metal complexes may be used in various layers of an OLED. The present invention therefore further provides an OLED comprising at least one inventive metal complex and for the use of at least one inventive metal complex in OLEDs. The inventive metal complexes are used preferably in the light-emitting layer, more preferably as emitter molecules. The present invention therefore further provides a light-emitting layer comprising at least one inventive metal complex as a matrix material or emitter molecule, preferably as an emitter molecule. Preferred inventive metal complexes have been specified above.

The inventive metal complexes may be present in bulk—without further additives—in the light-emitting layer or another layer of the OLED, preferably in the light-emitting layer. However, it is likewise possible and preferred that, in addition to the inventive metal complexes, further compounds are present in the layers, preferably in the light-emitting layer. For example, a fluorescent dye may be present in the light-emitting layer in order to alter the emission color of the inventive metal complex used as an emitter molecule. In addition—in a preferred embodiment—at least one matrix material may be used. Suitable matrix materials are known to those skilled in the art. In general, the matrix material is selected such that the band gap of the matrix material is greater than the band gap of the inventive metal complex used as an emitter. In the context of the present application, band gap is understood to mean the triplet energy. Suitable matrix materials for use with preference, especially in the case of use of inventive metal complexes as emitter materials which emit light in the blue region of the electromagnetic spectrum are, for example, carbene complexes, especially the carbene complexes specified in WO 2005/019373, WO 2005/0113704, WO 2006/018292, WO 2006/056418, WO 2007/115981, WO 2008/000726 and WO 2008/000727; disilylcarbazoles, for example 9-(4-tert-butylphenyl)-3,6-bis(triphenylsilylcarbazole), 9-(phenyl)-3,6-bis(triphenylsilyl)carbazole and the disilylcarbazoles specified in PCT application PCT/EP 2007/059648, which was yet to be published at the priority date of the present application, and the compounds detailed in WO 2004/095889, EP 1617710, EP 1617711, WO 2006/112265, WO 2006/130598.

The individual aforementioned layers of the OLED may in turn be composed of 2 or more layers. For example, the hole-transporting layer may be composed of one layer into which holes are injected from the electrode and one layer which transports the holes away from the hole-injecting layer into the light-emitting layer. The electron-transporting layer may likewise consist of a plurality of layers, for example one layer into which electrons are injected by the electrode and one layer which receives electrons from the electron-injecting layer and transports them into the light-emitting layer. These specified layers are each selected according to factors such as energy level, thermal resistance and charge carrier mobility, and also energy differential of the layers mentioned with the organic layers or the metal electrodes. Those skilled in the art are capable of selecting the structure of the OLEDs in such a way that it is adapted optimally to the inventive metal complexes used preferably as emitter substances.

In order to obtain particularly efficient OLEDs, the HOMO (highest occupied molecular orbital) of the hole-transporting layer should be aligned to the work function of the anode, and the LUMO (lowest unoccupied molecular orbital) of the electron-transporting layer aligned to the work function of the cathode.

The present application further provides an OLED comprising at least one inventive light-emitting layer. The further layers in the OLED may be composed of any material which is typically used in such layers and is known to those skilled in the art.

Suitable materials for the aforementioned layers (anode, cathode, hole and electron injection materials, hole and electron transport materials and hole and electron blocker materials, matrix materials, fluorescence and phosphorescence emitters) are known to those skilled in the art and are specified, for example, in H. Meng, N. Herron, *Organic Small Molecule Materials for Organic Light-Emitting Devices in Organic Light-Emitting Materials and Devices*, eds.: Z. Li, H. Meng, Taylor & Francis, 2007, Chapter 3, pages 295 to 411.

The anode (1) is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals include the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (1) comprises an organic material, for example polyaniline, as described, for example, in Nature, Vol. 357, pages 477 to 479

(Jun. 11, 1992). At least either the anode or the cathode should be at least partly transparent in order to be able to emit the light formed.

Suitable hole-transporting materials for the layer (2) of the inventive OLEDs are disclosed, for example, in Kirk-Othmer Encyclopedia of Chemical Technology, 4th Edition, Vol. 18, pages 837 to 860, 1996. Either hole-transporting molecules or polymers may be used as the hole-transporting material. Customarily used hole-transporting molecules are selected from the group consisting of 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4,4',4"-tris(N,N-diphenylamino)triphenylamine (TDTA) and porphyrin compounds, and also phthalocyanines such as copper phthalocyanines. Customarily used hole-transporting polymers are selected from the group consisting of polyvinylcarbazoles, (phenylmethyl)polysilanes, PEDOT (poly(3,4-ethylenedioxythiophene)), preferably PEDOT doped with PSS (polystyrenesulfonate), and polyanilines. It is likewise possible to obtain hole-transporting polymers by doping hole-transporting molecules into polymers such as polystyrene and polycarbonate. Suitable hole-transporting molecules are the molecules already mentioned above.

Suitable electron-transporting materials for the layer (4) of the inventive OLEDs include metals chelated with oxinoid compounds, such as tris(8-hydroxyquinolato)aluminum ($Alq_3$), compounds based on phenanthroline such as 2,9-dimethyl-4,7-diphenyl-1,10-phenanthroline (DDPA=BCP) or 4,7-diphenyl-1,10-phenanthroline (DPA) and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). The layer (4) may serve both to ease the electron transport and as a buffer layer or as a barrier layer in order to prevent quenching of the exciton at the interfaces of the layers of the OLED. The layer (4) preferably improves the mobility of the electrons and reduces quenching of the exciton.

Of the materials specified above as hole-transporting materials and electron-transporting materials, some can fulfill a plurality of functions. For example, some of the electron-conducting materials are simultaneously hole-blocking materials when they have a low-lying HOMO.

The charge transport layers may also be electronically doped in order to improve the transport properties of the materials used, in order firstly to make the layer thicknesses more generous (avoidance of pinholes/short circuits) and secondly to minimize the operating voltage of the device. For example, the hole-transporting materials may be doped with electron acceptors; for example, phthalocyanines or arylamines such as TPD or TDTA may be doped with tetrafluorotetracyanoquinodimethane (F4-TCNQ). The electron-transporting materials may, for example, be doped with alkali metals, for example $Alq_3$ with lithium. Electronic doping is known to those skilled in the art and is disclosed, for example, in W. Gao, A. Kahn, J. Appl. Phys., Vol. 94, No. 1, Jul. 1, 2003 (p-doped organic layers); A. G. Werner, F. Li, K. Harada, M. Pfeiffer, T. Fritz, K. Leo, Appl. Phys. Lett., Vol. 82, No. 25, Jun. 23, 2003 and Pfeiffer et al., Organic Electronics 2003, 4, 89-103.

The cathode (5) is an electrode which serves to introduce electrons or negative charge carriers. The cathode may be any metal or nonmetal which has a lower work function than the anode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used. In addition, lithium-comprising organometallic compounds or LiF may be applied between the organic layer and the cathode in order to reduce the operating voltage.

The OLED of the present invention may additionally comprise further layers which are known to those skilled in the art. For example, a layer which eases the transport of the positive charge and/or matches the band gaps of the layers to one another may be applied between the layer (2) and the light-emitting layer (3). Alternatively, this further layer may serve as a protective layer. In an analogous manner, additional layers may be present between the light-emitting layer (3) and the layer (4) in order to ease the transport of the negative charge and/or to match the band gaps between the layers to one another. Alternatively, this layer may serve as a protective layer.

In a preferred embodiment, the inventive OLED, in addition to the layers (1) to (5), comprises at least one of the further layers mentioned below:

a hole injection layer between the anode (1) and the hole-transporting layer (2);

a blocking layer for electrons and/or excitons between the hole-transporting layer (2) and the light-emitting layer (3);

a blocking layer for holes and/or excitons between the light-emitting layer (3) and the electron-transporting layer (4);

an electron injection layer between the electron-transporting layer (4) and the cathode (5).

As already mentioned above, it is, however, also possible that the OLED does not have all of the layers (1) to (5) mentioned; for example, an OLED having the layers (1) (anode), (3) (light-emitting layer) and (5) (cathode) is likewise suitable, in which case the functions of the layers (2) (hole-transporting layer) and (4) (electron-transporting layer) are assumed by the adjacent layers. OLEDs which have the layers (1), (2), (3) and (5) or the layers (1), (3), (4) and (5) are likewise suitable.

Those skilled in the art know how suitable materials have to be selected (for example on the basis of electrochemical investigations). Suitable materials for the individual layers and suitable OLED structures are known to those skilled in the art and disclosed, for example, in WO2005/113704.

Furthermore, each of the specified layers of the inventive OLED may be composed of two or more layers. In addition, it is possible that some or all of the layers (1), (2), (3), (4) and (5) have been surface-treated in order to increase the efficiency of charge carrier transport. The selection of the materials for each of the layers mentioned is preferably determined by obtaining an OLED having a high efficiency.

The inventive OLED can be produced by methods known to those skilled in the art. In general, the OLED is produced by successive vapor deposition of the individual layers onto a suitable substrate. Suitable substrates are, for example, glass or polymer films. For the vapor deposition, customary techniques may be used, such as thermal evaporation, chemical vapor deposition and others. In an alternative process, the organic layers may be coated from solutions or dispersions in suitable solvents, in which case coating techniques known to those skilled in the art are employed.

Compositions which, in addition to the at least one inventive metal complex, have a polymeric material in one of the layers of the OLED, preferably in the light-emitting layer, are generally applied as a layer by means of solution-mediated processes.

In general, the different layers have the following thicknesses: anode (1) from 500 to 5000 Å, preferably from 1000 to 2000 Å; hole-transporting layer (2) from 50 to 1000 Å, preferably from 200 to 800 Å; light-emitting layer (3) from 10 to 1000 Å, preferably from 100 to 800 Å; electron-transporting layer (4) from 50 to 1000 Å, preferably from 200 to 800 Å; cathode (5) from 200 to 10 000 Å, preferably from 300 to 5000 Å. The position of the recombination zone of holes and electrons in the inventive OLED and thus the emission spectrum of the OLED may be influenced by the relative thickness of each layer. This means that the thickness of the electron transport layer should preferably be selected such that the electron/hole recombination zone is within the light-emitting layer. The ratio of the layer thicknesses of the individual layers in the OLED is dependent upon the materials used. The layer thicknesses of any additional layers used are known to those skilled in the art.

Use of the inventive metal complexes in at least one layer of the inventive OLED, preferably as emitter molecule in the light-emitting layer of the inventive OLEDs, allows OLEDs with high efficiency to be obtained. The efficiency of the inventive OLEDs may additionally be improved by optimizing the other layers. For example, highly efficient cathodes such as Ca, Ba or LiF may be used. Shaped substrates and novel hole-transporting materials which bring about a reduction in the operating voltage or an increase in the quantum efficiency are likewise usable in the inventive OLEDs. Furthermore, additional layers may be present in the OLEDs in order to adjust the energy level of the different layers and to facilitate electroluminescence.

The inventive OLEDs may be used in all devices in which electroluminescence is useful. Suitable devices are preferably selected from stationary and mobile visual display units. Stationary visual display units are, for example, visual display units of computers, televisions, visual display units in printers, kitchen appliances and advertising panels, illuminations and information panels. Mobile visual display units are, for example, visual display units in cellphones, laptops, cameras, especially digital cameras, vehicles and destination displays on buses and trains.

In addition, the inventive metal complexes may be used in OLEDs with inverse structure. The inventive metal complexes are preferably used in these inverse OLEDs in turn in the light-emitting layer. The structure of inverse OLEDs and the materials customarily used therein are known to those skilled in the art.

The invention claimed is:

1. A metal complex, comprising a ligand of formula (I):

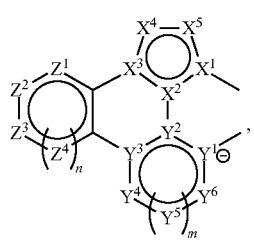

(I)

wherein:
$Y^5$ and $Z^4$ are each independently CD, $CR^1$, CH, or N;
D is deuterium;
$X^1$ is N;
$X^2, X^3, Y^1, Y^2,$ and $Y^3$ are each independently N or C;
$X^4$ is CD, $CR^1$, CH, N, $NR^1$, S or O;
$X^5$ is CD;
$Y^4$ and $Y^6$ are each independently CD, $CR^1$, CH, N, $NR^1$, S, or O;
$Z^1, Z^2,$ and $Z^3$ are each independently CD, $CR^1$, CH, or N;
$R^1$ is independently an unsubstituted or substituted alkyl, unsubstituted or substituted cycloalkyl, unsubstituted or substituted heterocycloalkyl, unsubstituted or substituted aryl, unsubstituted or substituted heteroaryl, unsubstituted or substituted alkenyl, unsubstituted or substituted cycloalkenyl, unsubstituted or substituted alkynyl, $SiR^2_3$, halogen, a substituent with donor or acceptor action, whereby, in the case that $R^1$ is bonded to a nitrogen atom, $R^1$ is independently an unsubstituted or substituted alkyl, unsubstituted or substituted aryl, or unsubstituted or substituted heteroaryl, whereby any two $R^1$ radicals together may additionally form an alkylene or arylene bridge;
$R^2$ is independently an unsubstituted or substituted alkyl, unsubstituted or substituted aryl, or unsubstituted or substituted heteroaryl;
m and n are each 1; and
wherein the metal complex comprises a deuterium atom.

2. The metal complex according to claim 1, wherein at least one of $X^4, Y^4, Y^5, Y^6, Z^1, Z^2, Z^3,$ and $Z^4$ is CD.

3. The metal complex according to claim 1, wherein at least one of $X^1$ and $Y^1$ is N.

4. The metal complex according to claim 1, wherein:
$X^1$ is N;
$X^2, Y^1, Y^2,$ and $Y^3$ are each C;
$X^3$ is C or N;
$X^4$ is $CR^1$, CD, N, $NR^1$, O, or S;
$X^5$ is CD;
$Y^4, Y^5,$ and $Y^6$ are each independently CH, CD, or $CR^1$; and
$Z^1, Z^2, Z^3,$ and $Z^4$ are each independently CH, CD, $CR^1$, or N.

5. The metal complex according to claim 3, wherein:
$X^1$ is N;
$X^4$ is CD or $CR^1$; and
$X^5$ is CD.

6. The metal complex according to claim 5, wherein:
$X^3$ is N;
$X^4$ and $Z^3$ are each $CR^1$; and
$Y^4, Y^5, Y^6, Z^1, Z^2,$ and $Z^4$ are each CD.

7. The metal complex according to claim 1, wherein:
$R^1$ is independently an unsubstituted or substituted alkyl, unsubstituted or substituted aryl, unsubstituted or substituted heteroaryl, $SiR^2_3$, F, $OR^2$, $SR^2$, $NR^2_2$, $CF_3$, or CN, whereby each $R^1$, in the case that $R^1$ is bonded to a nitrogen atom, is independently an unsubstituted or substituted alkyl or unsubstituted or substituted aryl; and
$R^2$ is independently an unsubstituted or substituted alkyl or unsubstitulted or substituted aryl.

8. The metal complex according to claim 1, wherein the metal complex has formula (II):

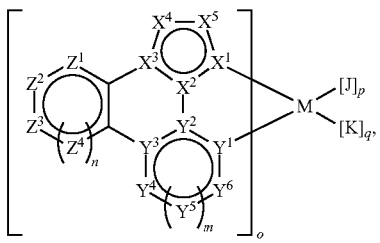

(II)

wherein:
M is a transition metal atom from group IB, IIB, IIIB, IVB, VB, VIB, VIIB, or VIII of the Periodic Table of the Elements (CAS version), in any oxidation state possible for the metal atom;
J is a mono- or dianionic ligand which is optionally mono- or bidentate;
K is an uncharged, mono- or bidentate ligand which is optionally photoactive;
o is 1, 2, 3, or 4, whereby o is 1, 2, or 3 when M is Ir(III), and is 1 or 2 when M is Pt(II) or Os(II);
p is 0, 1, 2, 3, or 4, whereby p is 0, 1, 2, 3, or 4 when M is Ir(III), and is 0, 1, or 2 when M is Pt(II) and Os(II), and p is a number of bonding sites to the metal atom M;
q is 0, 1, 2, 3, or 4, whereby q is 0, 1, or 2 when M is IR(III), is 0 or 1 when M is Pt(II), and is 2 or 3 when M is Os(II), and q is a number of bonding sites to the metal atom; and
wherein o, p, and q depend on the oxidation state and coordination number of the metal atom present and on charge of the ligands.

9. The metal complex according to claim 8, wherein the metal complex has formula (IIa):

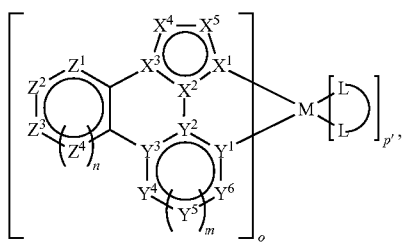

(IIa)

wherein:
M is a transition metal atom from group IB, IIB, IIIB, IVB, VB, VIB, VIIB, or VIII of the Periodic Table of the Elements (CAS version), in any oxidation state possible for the metal atom;

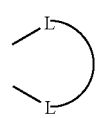

is a bidentate monoanionic ligand which optionally comprises a deuterium atom;
o is 1, 2, 3, or 4, whereby o is 1, 2, or 3 when M is Ir(III), and is 1 or 2 when M is Pt(II);
p' is 0, 1, or 2, whereby p' is 0, 1, or 2 when M is Ir(III), and is 0 or 1 when M is Pt(II), wherein p' is a number of

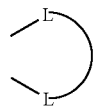

ligands; and
wherein o and p' depend on the oxidation state and coordination number of the metal atom present.

10. The metal complex according to claim 9, wherein L in the bidentate monoanionic ligand is in each case independently selected the group consisting of from O, N, and C.

11. The metal complex according to claim 9, wherein the metal complex has formula (IIaa):

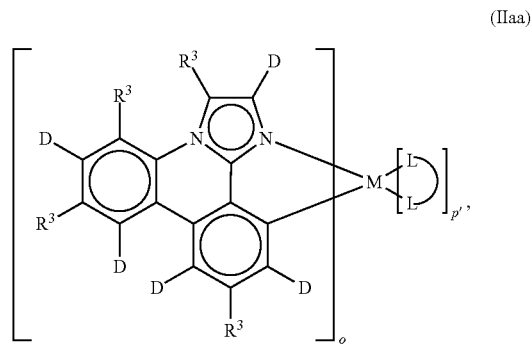

(IIaa)

wherein:
D is deuterium; and
$R^3$ is independently deuterium or $R^1$.

12. The metal complex according to claim 9, wherein:
M is Ir(III) or Pt(II);
o is 1, 2, or 3 when M is Ir(III), and is 1 or 2 when M is Pt(II);
p is 0, 1, or 2 when M is Ir(III); and is 0 or 1 when M is Pt(II); and
wherein a sum of o+p' is 3 when M is Ir(III) and is 2 when M is Pt(II), and o is at least 1.

13. An organic light-emitting diode, comprising a metal complex according to claim 1.

14. A light-emitting layer, comprising a metal complex according to claim 1.

15. An organic light-emitting diode, comprising a light-emitting layer according to claim 14.

16. A device, selected from the group consisting of a stationary visual display unit, an illumination, and a mobile visual display unit, comprising an organic light-emitting diode according to claim 13.

17. A device, selected from the group consisting of a stationary visual display unit, an illumination, and mobile visual display unit, comprising an organic light-emitting diode according to claim 15.

* * * * *